United States Patent
Udayampalayam Palanisamy et al.

(10) Patent No.: US 7,687,488 B2
(45) Date of Patent: Mar. 30, 2010

(54) 2-SUBSTITUTED METHYL PENAM DERIVATIVES

(75) Inventors: Senthilkumar Udayampalayam Palanisamy, Chennai (IN); Andrew Gnanaprakasam, Chennai (IN); Panchapakesan Ganapathy, Chennai (IN); Mukut Gohain, Chennai (IN); Venkatasubramanian Hariharan, Chennai (IN); Sriram Rajagopal, Chennai (IN); Maneesh Paul-Satyaseela, Chennai (IN); Shakti Singh Solanki, Chennai (IN); Sathishkumar Devarajan, Chennai (IN)

(73) Assignee: Orchid Chemicals & Pharmaceuticals Ltd., Chennai (IN)

(*) Notice: Subject to any disclaimer, the term of this patent is extended or adjusted under 35 U.S.C. 154(b) by 145 days.

(21) Appl. No.: 11/822,956

(22) Filed: Jul. 11, 2007

(65) Prior Publication Data

US 2008/0015156 A1    Jan. 17, 2008
US 2009/0093423 A2    Apr. 9, 2009

(30) Foreign Application Priority Data

Jul. 12, 2006   (IN) .................. 1217/CHE/2006

(51) Int. Cl.
A61K 31/43 (2006.01)
C07D 499/00 (2006.01)

(52) U.S. Cl. .................. 514/192; 514/195; 540/309

(58) Field of Classification Search .................. 540/200, 540/203, 302, 303, 310, 309; 514/192, 195
See application file for complete search history.

(56) References Cited

U.S. PATENT DOCUMENTS 4,562,073 A    12/1985  Micetich et al.
6,770,759 B2*  8/2004   Buynak et al. ............. 540/310

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta, Sudha R. "Crystalline Solids." Advanced Drug Delivery Reviews 48(2001): 3-26.*
Dorwald F. A. (Side Reactions in Organic Synthesis, 2005, Wiley: VCH, Weinheim p. IX of Preface. 19 pages total).*
National Committee for Clinical Laboratory Standards (NCCLS), "Methods for Dilution Antimicrobial Susceptibility Tests for Bacteria That Grow Aerobically," M7-A6, vol. 23, No. 2 (Jan. 2003).
Bebrone, Carine et al., "CENTA as a Chromogenic Substrate for Studying β-Lactamases," Antimicrobial Agents and Chemotherapy, vol. 45, No. 6, p. 1868-1871 (Jun. 2001).
Jamieson, Conor E. et al., "In Vitro and In Vivo Activities of AM-112, a Novel Oxapenem," Antimicrobial Agents and Chemotherapy, vol. 47, No. 5, p. 1652-1657 (May 2003).
Kuck, N.A. et al., "Comparative In Vitro and In Vivo Activities of Piperacillin Combined with the β-Lactamase Inhibitors Tazobactam, Clavulanic Acid, and Sulbactam," Antimicrobial Agents and Chemotherapy, vol. 33, No. 11, p. 1964-1969 (Nov. 1989).
Bryson, Harriet M. et al., "Piperacillin/Tazobactam A Review of its Antibacterial Activity, Pharmacokinetic Properties and Therapeutic Potential," Drugs, vol. 47, No. 3, p. 506-535 (1994).
Kriengkauykiat, Jane et al., "Use of an Efflux Pump Inhibitor To Determine the Prevalence of Efflux Pump-Mediated Fluoroquinolone Resistance and Multidrug Resistance in Pseudomonas Aeruginosa," Antimicrobial Agents and Chemotherapy, vol. 49, No. 2, p. 565-570 (Feb. 2005).

* cited by examiner

*Primary Examiner*—Kamal A Saeed
*Assistant Examiner*—Samantha L Shterengarts
(74) *Attorney, Agent, or Firm*—Oliff & Berridge, PLC (57) ABSTRACT

Novel 2-substituted methyl penam derivatives include the formula (I), their analogs, their tautomeric forms, their stereoisomers, their polymorphs, their solvates, their pharmaceutically acceptable salts, and pharmaceutical compositions containing them;

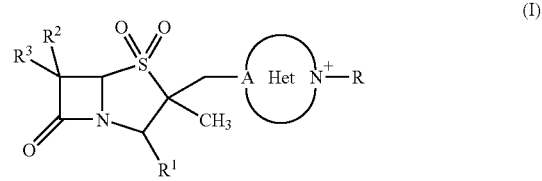

(I)

wherein A=C or N; Het is a three- to seven-membered heterocyclic ring; $R^1$ represents carboxylate anion, or —COOR$^4$ where $R^4$ represents hydrogen, carboxylic acid protecting group or a pharmaceutically acceptable salt; $R^2$ and $R^3$ may be same or different and independently represent hydrogen, halogen, amino, alkyl, protected amino, optionally substituted alkyl, alkenyl, alkynyl and the like; R represents substituted or unsubstituted alkyl, alkenyl, aryl, aralkyl, cycloalkyl, heterocyclyl or heterocyclylalkyl.

14 Claims, 1 Drawing Sheet

Figure 1: Comparison of IC$_{50}$ of Tazo with that of the novel compounds.

2-SUBSTITUTED METHYL PENAM DERIVATIVES

FIELD

Described are novel 2-substituted methyl penam derivatives of the formula (I), their analogs, their tautomeric forms, their stereoisomers, their polymorphs, their solvates, their pharmaceutically acceptable salts and esters/prodrugs thereof, (I)

wherein A=C or N; Het is a three- to seven-membered heterocyclic ring; $R^1$ represents carboxylate anion, or —$COOR^4$ wherein $R^4$ represents hydrogen, carboxylic acid protecting group or a pharmaceutically acceptable salt; $R^2$ and $R^3$ may be same or different and independently represent hydrogen, halogen, amino, protected amino, optionally substituted alkyl, alkenyl, alkynyl and the like; R represents substituted or unsubstituted alkyl, alkenyl, aryl, aralkyl, cycloalkyl, oxo, heterocyclyl or heterocyclylalkyl. The present invention further provides a process for preparing the compound of formula (I).

The novel compounds herein are useful as β-lactamase inhibitors, which enhance the antibiotic spectrum of a suitable antibiotic agent.

BACKGROUND

The β-lactam type antibiotics, namely penicillins and cephalosporins are frequently used antibiotics. It is known that β-lactamase produced by microorganisms hydrolyze the β-lactam ring thereby deactivating antibiotic activity. In order to reduce the effect of β-lactamase, the antibiotics are administered in combination with β-lactamase inhibitor. These inhibitors function by binding to the beta-lactamase enzymes more efficiently than the actual beta-lactam antibiotic itself. This combination allows the antibiotic to "do its job" without being degraded by the beta-lactamase enzymes. Several antibiotic/β-lactamase inhibitor combinations exist in the market for example, Ampicillin/Sulbactam, Amoxicillin/Clavulanate and Ticarcillin/Clavulanate. These β-lactam/β-lactamase inhibitor combination antibiotic are being used for the treatment of infections in the community and in the hospital setting.

Among many β-lactamase inhibitors that are known in the literature, compound of following formula is disclosed in U.S. Pat. No. 4,562,073, wherein $R^1$ is hydrogen or trialkylsilyl; $R^2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, gamma.-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1, 3-dioxoden-4-yl)methyl, $C_{8-13}$ benzoyloxyalkyl or group for forming a pharmaceutically acceptable salt; and $R^3$ has the same meaning as above $R_2'$. This patent describes a β-lactam inhibitor wherein $R^1=R^2=R^3=H$, which hereinafter referred as Tazo.

We have focused our research to identify novel β-lactamase inhibitors and succeeded with novel 2-substituted methyl penam derivatives of the formula (I). The novel 2-substituted methyl penam derivatives of the formula (I) are β-lactamase inhibitors used in combination with β-lactam antibiotics. The novel compounds herein in combination with suitable β-lactam antibiotic are effective against a number of human or animal pathogens and clinical isolates.

OBJECTIVE

One objective herein is to provide novel 2-substituted methyl penam derivatives of the formula (I).

Another objective herein is to provide a pharmaceutical composition with the novel 2-substituted methyl penam derivatives in combination with antibiotics.

Another objective herein is to provide a method of preventing or treating a bacterial infection in a host, typically an animal, and most typically a human, including administering to the host a therapeutic amount of compound of formula (I) of the novel compounds, or a pharmaceutically acceptable salt and/or prodrug therein along with β-lactam antibiotic.

Yet another objective herein is to provide a cost effective process for the preparation of 2-substituted methyl penam derivatives of the formula (I).

SUMMARY

Described are novel 2-substituted methyl penam derivatives of the formula (I), (I)

their derivatives, their analogs, their tautomeric forms, their stereoisomers, their polymorphs, their solvates, their pharmaceutically acceptable salts and esters and their pharmaceutically acceptable compositions, wherein A=C or N; Het is a three- to seven-membered heterocyclic ring; $R^1$ represents carboxylate anion, or —$COOR^4$ wherein $R^4$ represents hydrogen, carboxylic acid protecting group or a pharmaceutically acceptable salt; $R^2$ and $R^3$ may be same or different and independently represent hydrogen, halogen, amino, protected amino, optionally substituted alkyl, alkenyl, alkynyl and the like; R represents substituted or unsubstituted alkyl, alkenyl, aryl, aralkyl, cycloalkyl, oxo, heterocyclyl and heterocyclylalkyl.

BRIEF DESCRIPTION OF THE DRAWING

The FIG. 1 illustrates a comparison of $IC_{50}$ values of the novel compounds of Examples 1 to 7 compared with Tazo against Penicillanase enzyme.

DETAILED DESCRIPTION

Novel 2-substituted methyl penam derivatives are the formula (I), (I)

their derivatives, their analogs, their tautomeric forms, their stereoisomers, their polymorphs, their solvates, their pharmaceutically acceptable salts and esters and their pharmaceutically acceptable compositions thereof wherein:

A=C or N;

Het is a three- to seven-membered heterocyclic ring;

$R^1$ represents carboxylate anion, or —COOR$^4$ wherein R$^4$ represents hydrogen, carboxylic acid protecting group such as an alkyl, aryl, aralkyl and the like or a pharmaceutically acceptable salt;

$R^2$ and $R^3$ may be same or different and independently represent hydrogen, halogen, amino, protected amino, or optionally substituted alkyl, alkenyl, alkynyl, and the like;

R is represented by substituted or unsubstituted alkyl, alkenyl, aryl, aralkyl, cycloalkyl, oxo, heterocyclyl, heterocyclylalkyl groups and selected from linear or branched alkyl group such as methyl, ethyl, n-propyl, isopropyl, n-butyl, isobutyl, t-butyl, n-pentyl, isopentyl, hexyl, trifluoroethyl, diethoxyethyl, hydroxyethyl, hydroxypropyl, dihydroxypropyl and the like; alkenyl group such as vinyl, allyl, butenyl, and the like, aryl group such as phenyl, naphthyl and the like, the aryl group may be substituted; aralkyl group such as phenylmethyl, phenylethyl, naphthylmethyl, naphthylethyl and the like, the aralkyl group may be substituted; cycloalkyl, heterocyclyl group such as pyrrolidinyl, morpholinyl, thiomorpholinyl, piperidinyl, piperazinyl, imidazolyl, triazolyl and the like, heterocyclylalkyl, which may be substituted, and oxo group such as N—O wherein oxygen is further optionally substituted. Suitable substituent is selected from halo, alkyl, alkenyl, alkynyl, alkyloxy, allyl, cyano, nitro, carboxy, alkoxycarbonyl, amino, amide, sulfonyl, carbamoyl, aryl, aryloxy, heterocyclyl carbonyl, carboxylic acid and its derivatives such as esters, amides hydroxamic acids, and the like which in turn further substituted with alkoxycarbonylalkyl, hydroxyethyl, alkyl, aryl, heterocycyl, esters and the like.

Preferable R groups are selected from but not limited to —(CH$_2$)$_n$—CH$_3$, —(CH$_2$)$_n$C$_6$H$_5$, —(CH$_2$)$_n$—CH=CH$_2$, —CH$_2$—CONH$_2$, —CH$_2$COOBu$^t$, —(CH$_2$)$_n$CO— heterocyclyl, —CH$_2$—CONH—(CH$_2$)$_n$—COOEt, and the like, and the corresponding acids of the esters, where n is an integer ranging from 0 to 5. Described herein involves any substitution on heterocyclyl nitrogen(s) that is hitherto unreported hence novel.

Suitable groups represented by R$^4$ are selected from hydrogen, carboxylic acid protecting group such as an ester selected from methoxybenzyl, nitrobenzyl, silyl, alkyl, diphenylmethyl, proxetil, axetil, pivoxil, hexetil, daloxate and the like or a pharmaceutically acceptable salt.

Het represents a "heterocyclic group containing three- to seven-membered ring which may have suitable substituent(s)" and, especially preferable heterocyclic group may be heterocyclic group such as pyrrolyl, pyrrolinyl, imidazolyl, pyrazolyl, pyridyl, pyrimidinyl, pyrazinyl, piperadinyl, oxazolidinyl, thiazolyl, benzothiazolyl, purinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), pyrrolidinyl, imidazolidinyl, indolyl, benzimidazolyl, quinolyl, isoquinolyl, indazolyl, benzotriazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl. The defined heterocyclic groups may optionally be substituted with the same or different one or more substituents, suitable substituent(s) such as: lower alkyl (e.g. methyl, ethyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); hydroxy; halogen (e.g. chloro, bromo, etc.); amino; protected amino; cyano; nitro; carboxy; protected carboxy; sulfo; sulfamoyl; imino; oxo; amino(lower)alkyl (e.g. aminomethyl, aminoethyl, etc.); halogen, trihalomethyl (e.g. CF$_3$) and the like.

$R^2$ and $R^3$ may be same or different and independently represent hydrogen, halogen, amino, protected amino such as tritylamino, acylamino such as phenylacetylamino, phenoxyacetylamino, benzoylamino, and the like; optionally substituted alkyl, alkenyl, alkynyl and the like.

Novel penam derivatives of the following formula, their derivatives, their analogs, their tautomeric forms, their stereoisomers, their polymorphs, their solvates, their pharmaceutically acceptable salts/prodrugs and their pharmaceutically acceptable compositions thereof wherein:

$R^1$ represents carboxylate anion, or —COOR$^4$ wherein R$^4$ represents hydrogen, carboxylic acid protecting group or a pharmaceutically acceptable salt;

$R^2$ and $R^3$ may be same or different and independently represent hydrogen, halogen, amino, protected amino, optionally substituted alkyl, alkenyl, alkynyl and the like;

R is represented by substituted or unsubstituted alkyl, alkenyl, aryl, aralkyl, cycloalkyl, oxo, heterocyclyl, heterocyclylalkyl and the like.

Representative compounds include:
1. 1-{[(2S,3S,5R)-2-Carboxy-3-methyl-4,4,7-trioxo-4-thia-1-azabicyclo[3.2.0]hept-3-yl]methyl}-3-methyl-1H-1,2,3-triazol-3-ium;
2. 1-{[(2S,3S,5R)-2-Carboxy-3-methyl-4,4,7-trioxo-4-thia-1-azabicyclo[3.2.0]hept-3-yl]methyl}-3-ethyl-1H-1,2,3-triazol-3-ium;
3. 1-{[(2S,3S,5R)-2-Carboxy-3-methyl-4,4,7-trioxo-4-thia-1-azabicyclo[3.2.0]hept-3-yl]methyl}-3-n-propyl-1H-1,2,3-triazol-3-ium;
4. 1-{[(2S,3S,5R)-2-Carboxy-3-methyl-4,4,7-trioxo-4-thia-1-azabicyclo[3.2.0]hept-3-yl]methyl}-3-allyl-1H-1,2,3-triazol-3-ium;
5. 1-{[(2S,3S,5R)-2-Carboxy-3-methyl-4,4,7-trioxo-4-thia-1-azabicyclo[3.2.0]hept-3-yl]methyl}-3-(2-amino-2-oxoethyl)-1H-1,2,3-triazol-3-ium and the corresponding acid;
6. 1-{[(2S,3S,5R)-2-Carboxy-3-methyl-4,4,7-trioxo-4-thia-1-azabicyclo[3.2.0]hept-3-yl]methyl}-3-(2-t-butoxy-2-oxoethyl)-1H-1,2,3-triazol-3-ium and the corresponding acid;
7. 1-{[(2S,3S,5R)-2-Carboxy-3-methyl-4,4,7-trioxo-4-thia-1-azabicyclo[3.2.0]hept-3-yl]methyl}-3-(2-morpholin-4-yl-2-oxoethyl)-1H-1,2,3-triazol-3-ium and the corresponding acid;
8. 1-{[(2S,3S,5R)-2-Carboxy-3-methyl-4,4,7-trioxo-4-thia-1-azabicyclo[3.2.0]hept-3-yl]methyl}-3-{2[(2-ethoxy-2-oxoethyl)amino]-2-oxoethyl}-1H-1,2,3-triazol-3-ium and the corresponding acid;
9. 1-{[(2S,3S,5R)-2-Carboxy-3-methyl-4,4,7-trioxo-4-thia-1-azabicyclo[3.2.0]hept-3-yl]methyl}-3-{2-[(3-ethoxy-3-oxopropyl)amino]-2-oxoethyl}-1H-1,2,3-triazol-3-ium and the corresponding acid;
10. 1-{[(2S,3S,5R)-2-Carboxy-3-methyl-4,4,7-trioxo-4-thia-1-azabicyclo[3.2.0]hept-3-yl]methyl}-3-(2-{[1-(ethoxycarbonyl)-2-hydroxypropyl]amino}-2-oxoethyl)-1H-1,2,3-triazol-3-ium and the corresponding acid; and
11. 1-{[(2S,3S,5R)-2-Carboxy-3-methyl-4,4,7-trioxo-4-thia-1-azabicyclo[3.2.0]hept-3-yl]methyl}-3-benzyl-1H-1,2,3-triazol-3-ium.

According to another embodiment, there is provided a process for the preparation of novel 2-substituted methyl penam derivatives of the formula (I), which comprises:

reacting a compound of formula (II)

(I)

wherein A=C or N; Het is a three- to seven-membered heterocyclic ring; with a compound of formula (II b)

R—X       (II b)

wherein R is as defined above and X represents halogen to produce compound of formula (I) wherein all symbols are as defined above in presence or absence of silylating agent.

The compound of formula (II) is prepared according to the procedures available in the prior art, for example, the one disclosed in U.S. Pat. No. 6,936,711 as the reaction scheme shown below.

The conversion of compound of formula (II) to a compound of formula (I) may be carried out using silylating agent selected from hexamethyldisilazane (HMDS), trimethylchlorosilane (TMCS), trimethylsilyl iodide (TMSI), N,O-bis-(trimethylsilyl)-acetamide (BSA), methyltrimethylsilyltrifluoroacetamide (MSTFA), N,O-bistrimethylsilyltrifluoroacetamide (BSTFA), methyldichlorosilane, dimethyldichlorosilane, diphenyldichlorosilane, N-methylsilylacetamide (MSA), bistrimethylsilylurea and the like in the presence of solvents like acetone methanol, tetrahydrofuran, chloroform, dichloromethane, dichloroethane, ethylacetate, DMF, DMAc, and the like or a mixture thereof.

The novel compounds described herein are preferably formed as inner salts. When the representative substitution on R is carboxylic acid or amino group, it may be further converted to pharmaceutically acceptable salts. Bases used for making salts of carboxylic acid groups are selected from base such as sodium hydroxide, sodium methoxide, sodium bicarbonate, sodium carbonate, potassium bicarbonate, potassium carbonate, calcium hydroxide, magnesium hydroxide and the like, in solvents like ether, tetrahydrofuran, methanol, t-butanol, dioxane, isopropanol, ethanol, etc. Mixture of solvents may be used. Acid addition salts could also be prepared using appropriate acid.

Various polymorphs of compound of general formula (I) may be prepared by crystallization of compound of formula (I) under different conditions known in the prior art. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by Solid Probe NMR Spectroscopy, IR Spectroscopy, Differential Scanning Calorimetry, Powder X-ray Diffraction or such other techniques.

Pharmaceutically acceptable solvates of the compounds of formula (I) may be prepared by conventional methods such as dissolving the compounds of formula (I) in solvents such as water, methanol, ethanol, mixture of solvents such as acetone:water, dioxane: water, N,N-dimethylformamide:water and the like, preferably water and recrystallizing by using different crystallization techniques.

The novel compounds herein are useful for the treatment of microbial infections in humans and other warm blooded animals, under both parenteral and oral administration. In addition to the compounds of formula (I), the pharmaceutical compositions may also contain or be co-administered with one or more known drugs selected from other clinically useful antibiotic agents such as β-lactam antibiotics or aminoglycosides. The antibiotic agents are selected from Piperacillin, Ampicillin, Amoxicillin, Bacampicillin, Lenampicillin, Ticarcillin, Amikacin, Gentamycin, Tobramycin, Imipenem, Panipenem, Oxacillin, Aztreonam, Ceftriaxone, Cefbuperazone, Cephalotin, Cefazolin, Cefapirin, Ceftezole, Cefamandole, Cefotiam, Cefuroxime, Cefotaxime, Ceftizoxime, Cefmenoxime, Ceftriaxone, Cefuzoname, Ceftazidime, Cefoperazone, Cefsulodin, Cefoxtin, Cefmetazole, Latamoxef, Cefotetan, Cefbuperazone, Cefminox, Flomoxef, Cephalexin, Cefradine, Cefaclor, Cefadroxil, Cefprozil, Cefuroxime axetil, Cefotiam hexetil, Cefixime, Cefpodoxime proxetil, Ceftibuten, Cefetamet pivoxil, Cefdinir, Cefepime, and the like or derivatives thereof. These may include Penicillins such as Oxacillin or Flucloxacillin or Ampicillin; carbapenems such as Meropenem or Imipenem, Piperacillin and Cephalosporins like Ceftriaxone, Cefuperazone, to broaden the therapeutic effectiveness against, for example, Methicillin-Resistant staphylococci. Compounds of the formula (I) may also contain or be co-administered with bactericidal/permeability-increasing-g protein product (BPI) or efflux pump inhibitors to improve activity against gram negative bacteria and bacteria resistant to antimicrobial agents. Antiviral, antiparasitic, antifungal agents can also be administered in combination with the inhibitor compounds.

The pharmaceutical composition may be in the forms normally employed, such as tablets, capsules, pills, granules, powders, syrups, lozenges, solutions, suspensions, etc., and the like, may contain flavoring agents, sweeteners, etc. in suitable solid or liquid carriers or diluents, or in suitable sterile media to form injectable solutions or suspensions. The pharmaceutical composition may also contain pharmaceutically acceptable carrier that are known in the prior art.

The novel compounds can be lyophilized alone or in combination with antibiotic compounds/agents as described above optionally including any agents. The agents include complexing agents or anticoagulants, antioxidants, stabilizers, aminoglycosides, pharmaceutically acceptable salts or the like or mixtures thereof. The lyophilization can be performed for dilute solutions or concentrated solutions depending on the required quality of the final product. Prior to lyophilization or freeze-drying or thawing, the lyophilizate can be degassed to optimum concentration of gas. The compounds can be filtered under sterile condition. Appropriate filters such as ultrafiltration could also be used in order to reduce the levels of galactomannan substantially. The compounds of formula (I) could also be physically blended with a suitable antibiotic agent.

In addition to the novel compounds, the pharmaceutical composition may also contain buffers like sodium citrate, sodium acetate, sodium tartrate, sodium carbonate, sodium bicarbonate, morpholinopropanesulfonic acid, other phosphate buffers and the like and chelating agents like ethylenediaminetetraacetic acid (EDTA), diethylenetriaminepentaacetic acid, hydroxyethylenediaminetriacetic acid, nitrilotriacetic acid, 1,2-diaminocyclohexanetetraacetic acid, bis(2-aminoethyl)ethyleneglycoltetraacetic acid, 1,6-hexamethylenediaminetetraacetic acid and the like or pharmaceutically acceptable salts thereof. Novel compounds of Formula (I) are useful in treating a bacterial infection in a host, typically an animal, and most typically a human, including administering to the host a therapeutic amount of compound of formula (I) of the novel compounds, or a pharmaceutically acceptable salt and/or prodrug therein along with β-lactam antibiotic.

The examples below are provided by way of illustration only and should not be considered to limit the scope of the invention.

Example 1

Synthesis of 1-{[(2S,3S,5R)-2-Carboxy-3-methyl-4, 4,7-trioxo-4-thia-1-azabicyclo[3.2.0]hept-3-yl]methyl}-3-methyl-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (25 g) in acetone (100 mL) at 25-30° C. was added slowly N,O-bis(silylacetamide) (18.6 g) with stirring. The reaction mixture was stirred at this temperature (25-30° C.) for 15-20 min. To the clear solution obtained, methyl iodide (100 mL) was added over a period of 15 min. and stirred at 25-30 min. for 24 h. The precipitated solid was separated by filtration and washed with acetone (25 mL). Wet weight of the solid obtained was 30 g.

The above wet solid was stirred with purified water (300 mL) at 10-15° C. for 2.5 h. To the resulted reaction mixture was added sodium thiosulfate (0.1 g) and stirred at 10-15° C. for 10-15 min. To the reaction mixture, dichloromethane (300 mL) was added, stirred and the organic layer separated. The aqueous layer was washed with a solution of Amberlite LA-2 resin (5% solution in dichloromethane twice, followed by dichloromethane twice. To the aqueous solution, activated carbon (1 g) was added, stirred for 15 min, filtered and washed with purified water (25 mL). The solution was filtered and lyophilized to get the title compound in pure form (10 g). $^1$H NMR (400 MHz, DMSO) δ ppm: 1.39 (s, 3H), 3.14 (dd, J=16.0, 1.3 Hz, 1H), 3.55 (dd, J=16.0, 4.2 Hz, 1H), 3.97 (s, 1H), 4.34 (s, 3H), 5.05 (dd, J=4.2, 1.3 Hz, 1H), 5.29 (d, J=14.7 Hz, 1H), 5.42 (d, J=14.7 Hz, 1H), 8.91 (d, J=1.3 Hz, 1H), 8.99 (d, J=1.3 Hz, 1H). Mass m/z: M+1 peak at 315. Alternatively the solution could be subjected to spray-drying to yield the title compound.

Example 2

Synthesis of 1-{[(2S,3S,5R)-2-Carboxy-3-methyl-4,4,7-trioxo-4-thia-1-azabicyclo[3.2.0]hept-3-yl]methyl}-3-ethyl-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dichloromethane (100 mL) was added N,O-bis(silylacetamide) (10 g) and stirred for 30 min. at 25 to 30° C. To the clear solution was added iodoethane (52 g) during 20 min. at 25-30° C. under stirring. The reaction mixture was stirred at this temperature (25-30° C.) for 5 days. The precipitated solid was separated by filtration and washed with dichloromethane (30 mL). Wet weight of the solid obtained was 5 g.

The wet solid in purified water (30 mL) was stirred for 1 h at 10 to 15° C. To the clear solution was added sodium thiosulfate (0.05 g) and stirred at 10-15° C. for 10-15 min. To the reaction mixture, dichloromethane (30 mL) was added, stirred and the organic layer separated. The aqueous layer was washed with a solution of Amberlite LA-2 resin twice (5% solution in dichloromethane), followed by dichloromethane wash. To the aqueous solution, activated carbon (0.1 g) was added, stirred for 15 min, filtered and washed with purified water (10 mL). The solution was filtered and lyophilized to get the title compound in pure form (3 g). $^1$H NMR (400 MHz, DMSO) δ ppm: 1.39 (s, 3H), 1.52 (t, J=7.3 Hz, 3H), 3.14 (d, J=16.0 Hz, 1H), 3.55 (dd, J=16.0, 4.2 Hz, 1H), 3.99 (s, 1H), 4.69 (q, J=7.3 Hz, 2H), 5.05 (d, J=4.2 Hz, 1H), 5.30 (d, J=14.7 Hz, 1H), 5.43 (d, J=14.7 Hz, 1H), 9.00 (s, 1H), 9.04 (s, 1H). Mass m/z: M+1 peak at 329.

Example 3

Synthesis of 1-{[(2S,3S,5R)-2-Carboxy-3-methyl-4,4,7-trioxo-4-thia-1-azabicyclo[3.2.0]hept-3-yl]methyl}-3-n-propyl-1H-1,2,3-triazol-3-ium To a solution of 1-{[(2S,3S,5R)-2-carboxy-3-methyl-4,4,7-trioxo-4-thia-1-azabicyclo[3.2.0]hept-3-yl]methyl}-3-allyl-1H-1,2,3-triazol-3-ium (1 g; prepared as per Example 4) in water (50 mL) was added Pd/C (10%; 1 g) and the suspension hydrogenated under hydrogen pressure (4 kg) for 1 h at 25 to 30° C. After filtration the filtrate was lyophilized to get the title compound in pure form (1 g). $^1$H NMR (400 MHz, DMSO) δ ppm: 0.87 (t, J=6.9 Hz, 3H), 1.41 (s, 3H), 1.91-1.96 (m, 2H), 3.15 (d, J=16.0 Hz, 1H), 3.55 (d, J=16.0 Hz, 1H), 4.04 (s, 1H), 4.64 (t, J=5.9 Hz, 2H), 5.05 (s, 1H), 5.33 (d, J=14.4 Hz, 1H), 5.43 (d, J=14.4 Hz, 1H), 9.00 (s, 1H), 9.04 (s, 1H). Mass m/z: M+1 peak at 343.

Example 4

Synthesis of 1-{[(2S,3S,5R)-2-Carboxy-3-methyl-4,4,7-trioxo-4-thia-1-azabicyclo[3.2.0]hept-3-yl]methyl}-3-allyl-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dichloromethane (100 mL) was added N,O-bis(silylacetamide) (10 g) and stirred for 30 min. at 25 to 30° C. To the clear solution was added allyl bromide (28 g) during 20 min. at 25-30° C. under stirring. The reaction mixture was stirred at this temperature (25-30° C.) for 5 days. The precipitated solid was separated by filtration and washed with dichloromethane (50 mL). Wet weight of the solid obtained was 5 g.

The clear solution of above wet solid in purified water (30 mL) was stirred for 1 h at 10 to 15° C. To the reaction mixture, dichloromethane (300 mL) was added, stirred well and the organic layer separated. The aqueous layer was washed with a solution of Amberlite LA-2 resin twice, followed by dichloromethane wash. To the aqueous solution, activated carbon (1 g) was added, stirred for 15 min., filtered and washed with purified water (25 mL). The solution was filtered and lyophilized to get the title compound in pure form (2.5 g). $^1$H NMR (400 MHz, DMSO) δ ppm: 1.40 (s, 3H), 3.11 (d, J=16.0 Hz, 1H), 3.55 (dd, J=16.0, 4.2 Hz, 1H), 4.00 (s, 1H), 5.05 (d, J=4.2 Hz, 1H), 5.28-5.45 (m, 6H), 6.03-6.13 (m, 1H), 8.97 (s, 1H), 9.05 (s, 1H). Mass m/z: M+1 peak at 341.

Example 5

Synthesis of 1-{[(2S,3S,5R)-2-Carboxy-3-methyl-4,4,7-trioxo-4-thia-1-azabicyclo[3.2.0]hept-3-yl]methyl}-3-(2-amino-2-oxoethyl)-1H-1,2,3-triazol-3-ium

To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (5 g) in dimethylformamide (50 mL) was added N,O-bis(silylacetamide) (5.08 g) and stirred for 30 min. at 25 to 30° C. To the clear solution was added iodoacetamide (7.68 g) during 20 min. at 25-30° C. under stirring. The reaction mixture was heated to 50° C. and stirred at the same temp. for 28 h. Toluene (250 mL) was added at 25-30° C. and stirred for 1 h, the separated mass was dissolved in purified water (50 mL).

The clear solution was washed twice with dichloromethane (50 mL) and the aqueous layer was washed with solution of Amberlite LA-2 resin twice, followed by dichloromethane wash. To the aqueous solution, activated carbon (0.5 g) was added, stirred for 15 min, filtered and washed with purified water (12.5 mL). The solution was filtered and lyophilized to get the title compound (3 g). The crude product was purified with methanol and acetone mixture (1:5) to yield pure product (1 g). $^1$H NMR (400 MHz, DMSO) δ ppm: 1.36 (s, 3H), 3.17 (dd, J=16.1, 1.0 Hz, 1H), 3.55 (dd, J=16.1, 4.2 Hz, 1H), 4.06 (s, 1H), 4.98 (dd, J=4.2, 1.0 Hz, 1H), 5.33 (s, 2H), 5.45 (s, 2H), 7.67 (s, 1H), 8.03 (s, 1H), 8.87 (d, J=1.1 Hz, 1H), 8.92 (d, J=1.1 Hz, 1H). Mass m/z: M+1 peak at 358.

Example 6

Synthesis of 1-{[(2S,3S,5R)-2-Carboxy-3-methyl-4,4,7-trioxo-4-thia-1-azabicyclo[3.2.0]hept-3-yl]methyl}-3-(2-tert-butoxy-2-oxoethyl)-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dimethylformamide (100 mL) was added N,O-bis(silylacetamide) (15 g) and stirred for 30 min. at 25 to 30° C. To the clear solution was added t-butylbromo acetate (24 mL) during 20 min. at 25-30° C. under stirring. The reaction mixture was heated to 50° C. and stirred at the same temperature for 2 days. Diisopropylether (300 mL) was added at 25-30° C. and stirred for 1 h. The crude mass separated out was dissolved in purified water (100 mL).

The clear solution was washed twice with dichloromethane (50 mL) and the aqueous layer washed with solution of Amberlite LA-2 resin twice, followed by dichloromethane wash. To the aqueous solution, activated carbon (0.5 g) was added, stirred for 15 min., filtered and washed with purified water (15 mL). The solution was filtered and lyophilized to get the title compound (5 g) and the crude product was purified with methanol-acetone mixture (1:5) yielded pure product (2 g). $^1$H NMR (400 MHz, DMSO) δ ppm: 1.37 (s, 3H), 1.44 (s, 9H), 3.19 (d, J=16.0 Hz, 1H), 3.58 (dd, J=16.0, 4.2 Hz, 1H), 4.07 (s, 1H), 5.02 (d, J=4.2 Hz, 1H), 5.41 (s, 2H), 5.69 (s, 2H), 8.95 (s, 1H), 8.97 (s, 1H). Mass m/z: M+1 peak at 415.

Example 7

Synthesis of 1-{[(2S,3S,5R)-2-Carboxy-3-methyl-4,4,7-trioxo-4-thia-1-azabicyclo[3.2.0]hept-3-yl]methyl}-3-(2-morpholin-4-yl-2-oxoethyl)-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dimethylformamide (100 mL) was added N,O-bis(silylacetamide) (10 g) and stirred for 30 min. at 25 to 30° C. To the clear solution was added 4-(bromoacetyl)morpholine (14 g) during 20 min. at 25-30° C. under stirring. The reaction mixture was heated to 50° C. and stirred at the same temperature for 3 days. Diisopropylether (300 mL) was added to the reaction mixture at 25-30° C. and stirred for 1 h. The precipitated mass was separated out and dissolved purified water (100 mL).

Dichloromethane (100 mL) was added to the resultant clear solution, and stirred for 1 h at 10 to 15° C. and the organic layer separated. The aqueous layer was washed with freshly prepared solution of Amberlite LA-2 resin twice, followed by dichloromethane wash. To the aqueous solution, activated carbon (1 g) was added, stirred for 15 min., filtered and washed with purified water (25 mL). The solution was filtered and lyophilized to get the title compound (7 g). The crude product (0.5 g) was purified to obtain the pure title product (0.3 g). $^1$H NMR (400 MHz, DMSO) δ ppm: 1.36 (s, 3H), 3.15 (d, J=16.0 Hz, 1H), 3.43-3.67 (m, 9H), 3.97 (s, 1H), 5.06 (d, J=4.1 Hz, 1H), 5.37 (d, J=14.8 Hz, 1H), 5.49 (d, J=14.8 Hz, 1H), 5.94 (s, 2H), 8.87 (s, 1H), 8.97 (s, 1H). Mass m/z: M+1 peak at 428.

Example 8

Synthesis of 1-{[(2S,3S,5R)-2-Carboxy-3-methyl-4,4,7-trioxo-4-thia-1-azabicyclo[3.2.0]hept-3-yl]methyl}-3-{2[(2-ethoxy-2-oxoethyl)amino]-2-oxoethyl}-1H-1,2,3-triazol-3-ium

To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dimethylformamide (100 mL) was added N,O-bis(silylacetamide) (10 g) and stirred for 30 min. at 25 to 30° C. To the clear solution was added ethyl [(bromoacetyl)amino]acetate (19 g) during 20 min. at 25-30° C. under stirring. The reaction mixture was heated to 50° C. and stirred at the same temperature for 3 days. Diisopropylether (300 mL) was added to the reaction mixture at 25-30° C. and stirred for 1 h. The precipitated mass was separated and dissolved in purified water (100 mL).

The clear solution was washed twice with dichloromethane (100 mL) and stirred for 1 h at 10 to 15° C. and the organic layer was separated and washed with freshly prepared solution of Amberlite LA-2 resin twice, followed by dichloromethane wash. To the aqueous solution, activated carbon (1 g) was added, stirred for 15 min., filtered and washed with purified water (25 mL). The solution was filtered and lyophilized to get the title compound (4 g) and the 0.5 g of the lyophilized product was purified to get the title compound in pure form (0.25 g). $^1$H NMR (400 MHz, DMSO) δ ppm: 1.18 (t, J=7.0 Hz, 3H), 1.44 (s, 3H), 3.16 (d, J=15.9 Hz, 1H), 3.55 (dd, J=15.9, 4.2 Hz, 1H), 3.87-3.89 (m, 2H), 4.05-4.12 (m, 3H), 5.09 (d, J=4.2 Hz, 1H), 5.25 (d, J=14.3 Hz, 1H), 5.41 (d, J=14.3 Hz, 1H), 5.59 (s, 2H), 8.93 (s, 1H), 9.06 (s, 1H), 9.25 (t, J=5.4 Hz, 1H). Mass m/z: M+1 peak at 444.

Example 9

Synthesis of 1-{[(2S,3S,5R)-2-Carboxy-3-methyl-4,4,7-trioxo-4-thia-1-azabicyclo[3.2.0]hept-3-yl]methyl}-3-{2-[(3-ethoxy-3-oxopropyl)amino]-2-oxoethyl}-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (10 g) in dimethylformamide (100 mL) was added N,O-bis(silylacetamide) (10 g) and stirred for 30 min. at 25 to 30° C. To the clear solution was added ethyl 3-[(bromoacetyl)amino]propanoate (19 g) during 20 min. at 25-30° C. under stirring. The reaction mixture was heated to 50° C. and stirred at the same temperature for 3 days. Diisopropylether (300 mL) was added to the reaction mixture at 25-30° C. and stirring continued for 1 h. The precipitated mass was separated and dissolved in purified water (100 mL).

To the clear solution of the above crude mass in purified water (100 mL) was added dichloromethane (100 mL), stirred for 1 h at 10 to 15° C. and the organic layer separated. The aqueous layer was washed with freshly prepared solution of Amberlite LA-2 resin twice, followed by dichloromethane wash. To the aqueous solution, activated carbon (1 g) was added, stirred for 15 min., filtered and washed with purified water (25 mL). The solution was filtered and lyophilized to get the title compound (6 g) and the 0.5 g of the lyophilized product was purified to get the title compound in pure form (0.25 g). $^1$H NMR (400 MHz, DMSO) δ ppm: 1.18 (t, J=7.0 Hz, 3H), 1.44 (s, 3H), 2.51 (t, J=6.5 Hz, 2H), 3.16 (d, J=16.0 Hz, 1H), 3.37 (t, J=6.5 Hz, 2H), 3.57 (dd, J=16.0, 4.1 Hz, 1H), 4.03-4.08 (m, 3H), 5.09 (d, J=4.1 Hz, 1H), 5.24 (d, J=14.4 Hz, 1H), 5.40 (d, J=14.4 Hz, 1H), 5.47 (s, 2H), 8.85 (d, J=5.0 Hz, 1H), 8.90 (s, 1H), 9.00 (s, 1H). Mass m/z: M+1 peak at 458.

Example 10

Synthesis of 1-{[(2S,3S,5R)-2-Carboxy-3-methyl-4,4,7-trioxo-4-thia-1-azabicyclo[3.2.0]hept-3-yl]methyl}-3-(2-{[1-(ethoxycarbonyl)-2-hydroxypropyl]amino}-2-oxoethyl)-1H-1,2,3-triazol-3-ium To a suspension of (2S,3S,5R)-3-methyl-7-oxo-3-(1H-1,2,3-triazol-1-ylmethyl)-4-thia-1-azabicyclo-[3.2.0]heptane-2-carboxylic acid 4,4-dioxide (5 g) in dimethylformamide (50 mL) was added N,O-bis(silylacetamide) (10 g) and stirred for 30 min. at 25 to 30° C. To the clear solution was added ethyl 2-[(bromoacetyl)amino]-3-hydroxybutanoate (5.35 g) during 20 min. at 25-30° C. under stirring. The reaction mixture was heated to 50° C. and stirred at the same temperature for 3 days. Diisopropylether (100 mL) was added to the reaction mixture at 25-30° C. and stirring for 1 h. The precipitated mass was separated and dissolved in purified water (100 mL).

To the clear solution of the above crude mass in purified water (100 mL) was added dichloromethane (100 mL), stirred for 1 h at 10 to 15° C. and the organic layer separated. The aqueous layer was washed with freshly prepared solution of Amberlite LA-2 resin (5% solution in dichloromethane; 100 mL×2 times), followed by dichloromethane twice (2×300 mL). To the aqueous solution, activated carbon (1 g) was added, stirred for 15 min. filtered and washed with purified water (25 mL). The solution was filtered and lyophilized to get the title compound (1.1 g) and the 0.5 g of the lyophilized product was purified to get the title compound in pure form (0.15 g). $^1$H NMR (400 MHz, DMSO) δ ppm: 1.08 (d, J=6.3 Hz, 3H), 1.18 (t, J=7.0 Hz, 3H), 1.49 (s, 3H), 3.18 (d, J=16.0 Hz, 1H), 3.55 (dd, J=16.0, 3.5 Hz, 1H), 4.06-4.18 (m, 5H), 5.12 (d, J=3.5 Hz, 1H), 5.24 (d, J=14.2 Hz, 1H), 5.40 (d, J=14.2 Hz, 1H), 5.60 (d, J=14.8 Hz, 1H), 5.65 (d, J=14.8 Hz, 1H), 5.75 (d, J=6.6 Hz, 1H), 8.94 (s, 1H), 9.01 (d, J=7.0 Hz, 1H), 9.20 (s, 1H). Mass m/z: M+1 peak at 488.

Example 11

Synthesis of 1-{[(2S,3S,5R)-2-Carboxy-3-methyl-4,4,7-trioxo-4-thia-1-azabicyclo[3.2.0]hept-3-yl]methyl}-3-benzyl-1H-1,2,3-triazol-3-ium To a suspension of (2S,3S,5R)-3-Methyl-7-oxo-3-(1H-1,2,3-triazol-1-ylmethyl)-4-thia-1-azabicyclo-[3.2.0]heptane-2-carboxylic acid 4,4-dioxide (25 g) in acetone (100 mL) at 25-30° C. was added N,O-bis(silylacetamide) (18.6 g) in 20 min. at 25-30° C. under stirring. The reaction mixture was stirred at this temperature (25-30° C.) for 15-20 min. To the resulted clear solution was added benzyl bromide (100 mL) over a period of 15 min. and stirred at 25-30 min. for 24 h. The precipitated solid was separated by filtration and washed with acetone (25 mL). Wet weight of the solid obtained was 35 g.

To wet solid (35 g) was stirred with purified water (300 mL) at 10-15° C. for 2.5 h. To the reaction mixture, dichloromethane (300 mL) was added, stirred and the organic layer separated. The aqueous layer was washed with a solution of Amberlite LA-2 resin in dichloromethane, followed by dichloromethane twice. To the aqueous solution, activated carbon (1 g) was added, stirred for 15 min., filtered and washed with purified water (25 mL). The solution was filtered and lyophilized to get the title compound in pure form (10 g).
$^1$H NMR (400 MHz, DMSO) δ ppm: 1.37 (s, 3H), 3.13 (d, J=16.0 Hz, 1H), 3.54 (dd, J=16.0, 4.2 Hz, 1H), 3.98 (s, 1H), 5.04 (d, J=4.2 Hz, 1H), 5.30 (d, J=14.7 Hz, 1H), 5.43 (d, J=14.7 Hz, 1H), 5.91 (d, J=14.7 Hz, 1H), 5.96 (d, J=14.7 Hz, 1H), 7.41-7.46 (m, 5H), 9.03 (s, 1H), 9.04 (s, 1H). Mass m/z: M+1 peak at 391.

Testing

The novel compounds are assessed in combination with β-lactam antibiotic for their potential as β-lactamase inhibitors. The compounds described herein are initially assessed in vitro, the promising candidates are selected for further assessment in vivo, and then candidates are selected for pharmacokinetics study. In general, in vitro studies are initially performed, followed by in vivo assays. The novel penam derivatives having a substitution on the heterocyclyl nitrogen atom(s) shows significant β-lactamase inhibiting properties. For comparative studies, Tazo was used along with an antibiotic. For the biological studies, Piperacillin was chosen as an antibiotic agent.

In Vitro Antimicrobial Testing (MIC)

The novel compounds were tested for the in vitro antibacterial activities by the Agar Dilution Method as specified in documents published by NCCLS, now CLSI, USA. (National Committee for Clinical Laboratory Standards (NCCLS). 2003. Approved standard M7-A6. NCCLS, Villanova, Pa.).

Briefly, Stock solution (e.g. 8 mg/mL) of Piperacillin was made in 0.1 M Phosphate buffer, pH 6.0 and the solution was serially two fold diluted in the same buffer. Tazo was also dissolved in same buffer to get a solution of, e.g., 1 mg/mL. Novel penam derivatives described herein were dissolved in water to get a solution of, e.g., 1 mg/mL. Piperacillin was screened in a concentration range of 0.25-128 μg/mL. For combination, Tazo or the novel derivatives described herein were tested at a fixed concentration of 1, or 2, or 4 μg/mL along with the Piperacillin concentration ranging from 0.25 μg/mL to 128 μg/mL.

Piperacillin alone and in combination with the novel compounds or Tazo from each concentration was added to 20 mL of molten Mueller Hinton agar that had been cooled to 40-50° C. and poured in petridishes. The novel compounds and Tazo were also tested individually. The bacterial inoculum was prepared by picking 3 to 5 well-isolated bacterial colonies with the same morphological appearance from an 18-24 h old culture and adjusting the turbidity of the saline suspension to 0.5 McFarland Turbidity Standard equivalent to a bacterial population of $1.5 \times 10^8$ colony forming units (CFU) per mL of suspension. The suspension was diluted 1:10 in saline (i.e. 0.5 mL suspension+4.5 mL saline) to get a bacterial population of $1.5 \times 10^7$ CFU/mL as inoculum. This bacterial inoculum was inoculated onto petridishes containing Mueller Hinton Agar which had earlier been incorporated with different dilutions of Piperacillin or Piperacillin/Tazo or Piperacillin/novel compounds by a Multipoint Inoculator with each inoculum spot containing approximately $1 \times 10^4$ colony forming units (CFU) of the test bacterial strain. The inoculated petridishes were incubated at 35° C. in an ambient atmosphere for 16-20 h. The petridishes after incubation, were placed on a dark non-reflecting surface and the Minimum Inhibitory Concentration (MIC) recorded as the concentration, which showed no growth of the inoculated culture.

β-Lactamase Assay:

Representative novel compounds were subjected to β-lactamase assay to determine and compare their $IC_{50}$ with that of Tazo as described elsewhere (Bebrone et. al, 2001, *Antimicrob. Agents. Chemother.* 45(6): 1868-1871; Jamieson et. al, 2003, *Antimicrob. Agents. Chemother.* 47(5): 1652-1657). Briefly enzyme inhibition assays with Tazo acid as the standard inhibitor for % inhibitions & $IC_{50}$ value with optimized concentrations of Penicillinase enzyme & Centa β-lactamase substrate were performed.

Minimum Bactericidal Activity:

Minimum bactericidal studies were performed by broth macrodilution technique as described by NCCLS.

In Vivo Efficacy Studies:

Therapeutic effects were assessed in mice infected with bacteria that produce β-lactamase and resistant to Piperacillin. The efficacy studies were performed as described earlier (Kuck et al, 1989, *Antimicrob. Agents. Chemother.* 33(11): 1964-1969). Briefly, Swiss albino mice, 20+2 g, from in-house breeding facility were challenged by the intraperitoneal injection of bacterial suspensions in 0.5 mL of hog gastric mucin (10 to 100 50% lethal doses). Four or five dose levels of Piperacillin and the novel β-lactamase inhibitor compound (one representative compound-1) in combinations of 4:1 were administered either intravenously at 0.75 h and 4 h post infection for one day, or were prepared in 0.2% aqueous agar and administered subcutaneously once at 0.5 h post infection. All the untreated control animals died within 48 h of infection. In each experiment, in-house Tazo was used as an inhibitor control in four doses. Median (50%) effective dose ($ED_{50}$) were determined by applying the Reed and Muench's method of the 7-day survival ratios.

The in vitro studies showed that Piperacillin in combination with the novel compounds showed better antibacterial activity at lower concentrations of compounds described herein (1 μg/mL) including against those strains where Tazo did not potentate Piperacillin (Table 1). At 2 μg/mL and at 4 μg/mL the novel compounds potentiated Piperacillin in its antibacterial activity similar to that in combination with Tazo. At 1 μg/mL, the novel compounds (1, 2, 3, 4, and 5) potentiated Piperacillin 8 to 16 fold times better than when in combination with Tazo against the four strains—*E. coli* MRO 10002, *E. cloacae* MRO 11802, *K. pneumoniae* MRO 11007, *K. pneumoniae* MRO 11008.

TABLE 1

Comparison of MIC (µg/mL) of Piperacillin in combination with standard Tazo acid (Tazo) and Novel Inhibitor-compounds against Gram-negative clinical isolates

|  | Tazo | MIC of Piperacillin with Tazo or compounds described herein at 1 µg/mL |  |  |  |  |  |  |  |  |
|---|---|---|---|---|---|---|---|---|---|---|
|  |  | Example No. | | | | | | | | |
| Bacterial strains |  | 1 | 2 | 3 | 4 | 5 | 6 | 7 | 8 | 9 |
| E. coli 10003 | 32 | 4 | 4 | 8 | 4 | 8 | 32 | 32 | 16 | 16 |
| E. coli 10004 | 16 | 2 | 2 | 2 | 1 | 2 | 8 | 8 | 4 | 8 |
| E. coli 10001 | 16 | 2 | 4 | 4 | 4 | 4 | 8 | 8 | 4 | 8 |
| E. coli 10002 | 128 | 4 | 8 | 16 | 8 | 8 | >128 | >128 | 128 | >128 |
| E. coli 10006 | 2 | 1 | 1 | 2 | 1 | 2 | 4 | 8 | 4 | 8 |
| E. coli 10007 | 1 | 1 | 1 | 2 | 1 | 1 | 4 | 16 | 4 | 8 |
| K. pneumoniae 11006 | 32 | 8 | 8 | 8 | 8 | 8 | 32 | 16 | 16 | 16 |
| K. pneumoniae 11007 | >128 | 8 | 16 | 16 | 8 | 8 | >128 | >128 | 32 | 64 |
| K. pneumoniae 11008 | >128 | 4 | 8 | 8 | 8 | 8 | >128 | >128 | 128 | >128 |
| K. pneumoniae 11009 | 16 | 4 | 4 | 8 | 8 | 8 | 32 | 16 | 8 | 8 |
| K. pneumoniae 11010 | 2 | 2 | 2 | 2 | 2 | 2 | 2 | 4 | 2 | 2 |
| K. pneumoniae 11012 | 2 | 2 | 2 | 2 | 2 | 2 | 2 | 4 | 4 | 4 |
| C. freundii 12301 | 16 | 4 | 2 | 4 | 2 | 4 | 8 | 64 | 4 | 16 |
| C. sedlakii 12303 | 1 | 2 | 2 | 2 | 2 | 2 | 2 | 1 | 2 | 2 |
| P. aeruginosa 15019 | 32 | 16 | 16 | 16 | 16 | 16 | 32 | 32 | 32 | 32 |
| P. aeruginosa 15020 | 64 | 32 | 32 | 32 | 32 | 32 | 64 | 32 | 32 | 64 |
| P. aeruginosa 15021 | 32 | 32 | 32 | 32 | 32 | 32 | 32 | 32 | 32 | 32 |
| M. morganii 13701 | 16 | 8 | 8 | 32 | 8 | 8 | 16 | 8 | 8 | 8 |
| M. morganii 13702 | <0.25 | 0.5 | 0.5 | <0.25 | 0.5 | 0.5 | 0.5 | 2 | 2 | 2 |
| E. cloacae 11801 | 2 | 2 | 2 | 2 | 2 | 2 | 2 | 2 | 4 | 2 |
| E. cloacae 11802 | 64 | 2 | 2 | 4 | 2 | 2 | 32 | 32 | 16 | 16 |
| S. odonifera 13801 | 2 | 2 | 2 | 2 | 2 | 2 | 2 | 2 | 2 | 2 |
| A. baumanii 14501 | 8 | 16 | 8 | 16 | 8 | 8 | 16 | 8 | 8 | 8 |
| M. catarrhalis ATCC 43617 | <0.25 | <0.25 | <0.25 | <0.25 | <0.25 | <0.25 | <0.25 | <0.25 | <0.25 | <0.25 |
| M. catarrhalis ATCC 43627 | <0.25 | <0.25 | <0.25 | <0.25 | <0.25 | <0.25 | <0.25 | <0.25 | <0.25 | <0.25 |
| K. pneumoniae ATCC 700603 | 16 | 16 | 16 | 16 | 16 | 16 | 16 | 16 | 16 | 32 |
| E. coli ATCC 25922 | 2 | 2 | 2 | 2 | 2 | 2 | 2 | 2 | 2 | 2 |
| P. aeruginosa ATCC 27853 | 4 | 2 | 4 | 2 | 4 | 2 | 2 | 2 | 2 | 2 |

Strains that are boldfaced are uncharacterized-ESBL clinical strains.
All strain IDs except the ATCC strains are clinical isolates Microbial Research Orchid IDs (MRO: Library of clinical strains at Orchid Research Laboratories Ltd. (ORLL)).

Tazo is reported to be inactive against the ESBLs types SHV-3 and SHV-4 (Bryson H. M., and Brogden R. N, 1994, *Drugs*, 47(3): 506-535). When compared, the potentiation of Piperacillin's antibacterial activity of the novel compound described in Example 1 and Tazo (Table 2), it was observed that at 1 µg/mL and at 2 µg/mL the novel compound described in Example 1 potentiated Piperacillin>16 fold and >32 fold respectively, against both—SHV-3 and SHV-4 ESBL producing strains compared to Tazo. At 4 µg/mL the novel compound described in Example 1 potentiated Piperacillin>64 fold against the SHV-3 producing strain compared to Tazo, while it is comparable with Tazo against the SHV-3 producing strain at this concentration. At 1 µg/mL and 2 µg/mL, the novel compound described in Example 1, potentiated Piperacillin 2-16-fold compared to Tazo against the strains producing the TEM type ESBLs (TEM-10, TEM-12 and TEM-10 and -12).

TABLE 2

Comparison of MIC (μg/mL) of Piperacillin in combination with standard Tazo and Novel Inhibitor compounds against specific Extended spectrum β-lactamase (ESBLs) producing Gram-negative isolates from ATCC

| ATCC strains | ESBL Pheno type↓ | MIC of Piperacillin with different concentrations of Tazo or compound of Example 1 Inhibitor Conc.: | | | | | |
|---|---|---|---|---|---|---|---|
| | | 1 μg/mL | | 2 μg/mL | | 4 μg/mL | |
| | | Tazo | Example 1 | Tazo | Example 1 | Tazo | Example 1 |
| *E.coli* BAA-201 | TEM-3 | 4 | 4 | 4 | 2 | 2 | 2 |
| *E.coli* BAA-196 | TEM-10 | 64 | *8* | 16 | *4* | 4 | 4 |
| *E.coli* BAA-197 | *TEM-12* | 64 | *4* | 8 | *4* | 4 | 4 |
| *K.pneumoniae* 51503 | *TEM-10 &-12* | >128 | *32* | >128 | *16* | 16 | 8 |
| *E.coli* BAA-198 | TEM-26 | 4 | 4 | 4 | 4 | 4 | 2 |
| *P.mirabilis* BAA-663 | TEM-89 | 8 | 16 | 8 | 8 | 4 | 8 |
| *E.coli* BAA-202 | SHV-1 | >128 | >128 | >128 | >128 | >128 | >128 |
| *E.coli* BAA-199 | *SHV-3* | >128 | *8* | >128 | *4* | >128 | *2* |
| *E.coli* BAA-200 | *SHV-4* | >128 | *8* | >128 | *4* | 4 | 2 |
| *K.pneumoniae* 700603 | SHV-18 | 16 | 16 | 16 | 16 | 16 | 16 |

Figure 1:
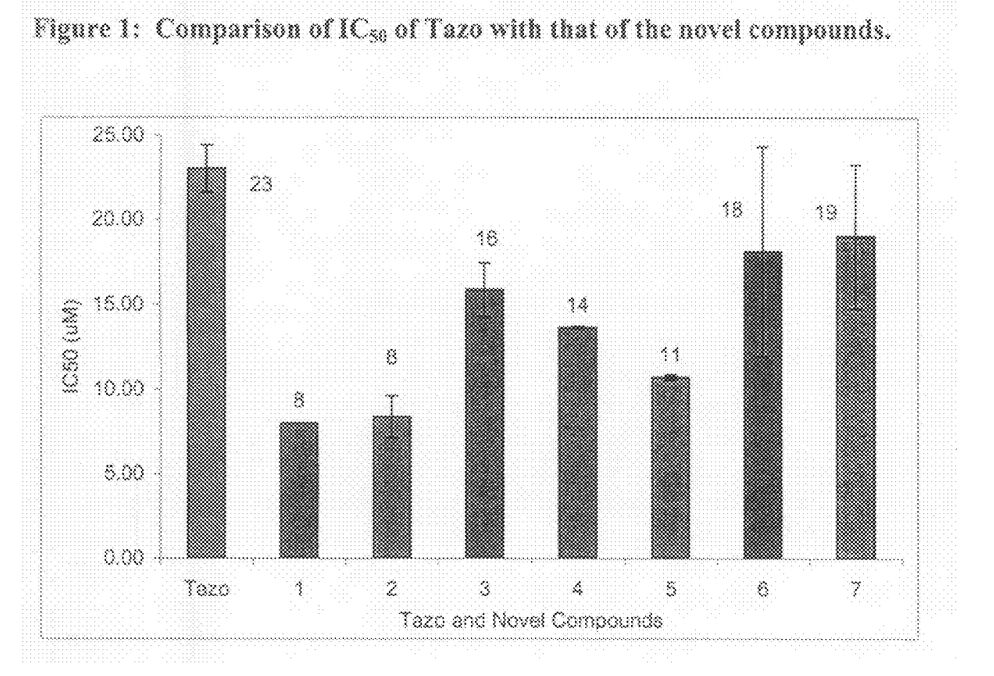

The IC$_{50}$ values of the novel compounds were compared with those of Tazo against Penicillinase enzyme (FIG. 1). The IC$_{50}$ values of the novel compounds described in Examples 1 and 2 was three-fold lower than those of standard Tazo, and in compounds described in Examples 3, 4, 5, 6 and 7 were comparatively lower than that of Tazo standard. These observations indicate the increased potency of the novel compounds compared to Tazo.

A study demonstrated that the strains resistant to Fluoroquinolones showed cross-resistance to Piperacillin/Tazo combination (86%), and to Ceftazidime (76%) (Kriengkauykiat et al. 2005, *Antimicrob Agents Chemother.* 49(2): 565-570). We compared the MIC of Piperacillin in combination with the novel compound described in Example 1 against the strains that were resistant to Ceftazidime, Ciprofloxacin, and Piperacillin/Tazo combination. We observed that these strains were susceptible to Piperacillin in combination with the compound described in Example 1. At 4 μg/mL the compound described in Example 1 potentiated the antibacterial activity of Piperacillin 2-16 fold compared to that of Tazo against the strains that are resistant to Ceftazidime and Ciprofloxacin. This may indicate that cross-resistance did not occur against the Example 1 compound when compared to Tazo standard (Table 3).

TABLE 3

Comparison of MIC (μg/mL) of Piperacillin (Pip) in combination with novel Inhibitor compound as described in Example 1 against Gram-negative clinical isolates that are resistant to its combination with standard Tazo, or alone against Ceftazidime and Ciprofloxacin

| S. No. | Organisms | Ceftazidime | Ciprofloxacin | Pip + 4 μg/mL Tazo | Pip + 4 μg/mL Example 1 |
|---|---|---|---|---|---|
| 1 | *E. coli* MRO 10135 | >64 | >16 | >128 | 16 |
| 2 | *A. baumani* MRO 14512 | >64 | >16 | 64 | 4 |
| 3 | *A. baumani* MRO 14514 | >64 | >16 | 64 | 32 |
| 4 | *A. baumani* MRO 14515 | >64 | >16 | 128 | 32 |

The values in the combination columns refer to that of Piperacillin in combination with 4 μg/mL inhibitor.

Minimum bactericidal concentration studies of Piperacillin either alone or in combination with Tazo or with Example 1 showed that Piperacillin remained bacteriostatic.

In vivo efficacy studies against the ESBL producing *E. coli* strains that have MIC of Piperacillin similar in both the compounds described in Example 1 and Tazo, revealed an ED$_{50}$ of Piperacillin in combination with the compound described in Example 1, two-fold lower compared to that in combination with Tazo (Table 4). When tested against the ESBL producing *K. pneumoniae* strain which is resistant in vitro to Piperacillin in combination with 1 μg/mL Tazo, compound described in Example 1 increases the efficacy of Piperacillin three-fold, which in vitro potentiates Piperacillin 16-fold at 1 μg/mL. These observations indicate that though the in vitro activity of compound described in Example 1 is comparable with Tazo, the in vivo efficacy of compound described in Example 1 is superior to that of Tazo.

TABLE 4

Comparison in In vivo efficacy at 4:1 ratio of Piperacillin in combination with Tazo, and with compound described in Example 1. Comparison of $ED_{50}$ of Piperacillin in combination with Tazo or compound obtained from Example 1 (mg/kg b.w.)

| ESBL positive strains | $ED_{50}$ of Piperacillin with Tazo | $ED_{50}$ of Piperacillin with Example 1 |
|---|---|---|
| E. coli MRO 10006 | 37.22 | 22.62 |
| E. coli MRO 10007 | 58.81 | 24.88 |
| K. pneumoniae MRO 11008 | 99.48 | 34.89 |

The values refer to Piperacillin at a ratio off 4:1 with the inhibitor.

Pharmacokinetic Study

1. Determination of the Possibility of Conversion of the Compound Obtained According to Example 1 to Tazo The compound of Example 1 was administered to Swiss mice at a dose of 8 mg/kg along with Piperacillin (32 mg/kg). Blood samples were collected at different time points. These samples were processed and analyzed by LC-MS/MS, which has the capability of simultaneously detecting even the lower concentration of Tazo (20 ng/mL) and the compound obtained from Example 1 (10 ng/mL).

2. Intravenous Pharmacokinetics of the Compound Obtained from Example 1 and Tazo in Mice The compound obtained from Example 1 and Tazo were administered to different groups of Swiss mice at a dose of 8 mg/kg along with Piperacillin (32 mg/kg). Blood samples were collected at different time points. These samples were processed and analyzed by HPLC.

LC-MS/MS analysis of the plasma samples did not show any detectable level of Tazo, which clearly indicated that the compound described in Example 1 did not get converted to Tazo after intravenous administration of compound described in Example 1 to mice.

TABLE 5

Intravenous pharmacokinetic parameters of compound obtained from Example 1 and Tazo in mice

| Parameters | Example 1 | Tazo |
|---|---|---|
| $AUC_{0-4\,h}$ (µg.h/mL) | 5.371 | 2.138 |
| $AUC_{0-\infty}$ (µg.h/mL) | 5.829 | 2.210 |
| $C_0$ (µg/mL) | 15.21 | 12.47 |
| Elimination half-life (h) | 0.272 | 0.269 |

It is evident from the table that the systemic exposure of the compound described in Example 1 is higher than that of Tazo.

We claim:

1. 2-Substituted methyl penam compounds of the formula (I), their tautomeric forms, their stereoisomers, and their pharmaceutically acceptable salts, wherein:

A=C or N;

Het is a five- to six-membered heterocyclic ring;

$R^1$ represents carboxylate anion, or —COOR$^4$ wherein $R^4$ represents hydrogen, carboxylic acid protecting group or a pharmaceutically acceptable salt;

$R^2$ and $R^3$ may be same or different and independently represent hydrogen, halogen, amino, protected amino, optionally substituted alkyl, alkenyl, alkynyl; and R is represented by substituted or unsubstituted alkyl, alkenyl, aryl, aralkyl, cycloalkyl, oxo, heterocyclyl or heterocyclylalkyl.

2. Penam compounds of the following formula, their tautomeric forms, their stereoisomers, their pharmaceutically acceptable salts and their pharmaceutically acceptable compositions thereof wherein:

$R^1$ represents carboxylate anion, or —COOR$^4$ wherein $R^4$ represents hydrogen, carboxylic acid protecting group or a pharmaceutically acceptable salt;

$R^2$ and $R^3$ may be same or different and may and independently represent hydrogen, halogen, amino, protected amino, optionally substituted alkyl, alkenyl, alkynyl; and R is represented by substituted or unsubstituted alkyl, alkenyl, aryl, aralkyl, cycloalkyl, oxo, heterocyclyl or heterocyclylalkyl.

3. The penam compounds according to claim 1 wherein, R is represented by substituted or unsubstituted groups selected from linear or branched alkyl group comprising methyl, ethyl, n-propyl, isopropyl, n-butyl, isobutyl, t-butyl, n-pentyl, isopentyl, hexyl, trifluoroethyl, diethoxyethyl, hydroxyethyl, hydroxypropyl, dihydroxypropyl, isopropyl, and t-butyl; alkenyl group comprising vinyl, allyl and butenyl, aryl group comprising phenyl and naphthyl; aralkyl group comprising phenylmethyl, phenylethyl, naphthylmethyl and naphthylethyl; cycloalkyl, heterocyclyl group comprising pyrrolidinyl, morpholinyl, thiomorpholinyl, piperidinyl, piperazinyl, imidazolyl and triazolyl; heterocyclylalkyl; oxo and optionally substituted oxo; the substituents are selected from halo, alkyl, alkenyl, alkynyl, alkyloxy, allyl, cyano, nitro, carboxy, alkoxycarbonyl, amino, amide, sulfonyl, carbamoyl, aryl, aryloxy, heterocyclyl carbonyl, carboxylic acid and its derivatives comprising esters, amides and hydroxamic acid; the substituents are further substituted with alkoxycarbonylalkyl, hydroxyethyl, alkyl, ester and the corresponding hydrolyzed acid, aryl and heterocycyl.

4. The penam compounds according to claim 1 wherein R groups selected from —(CH$_2$)$_n$—CH$_3$, —(CH$_2$)$_n$C$_6$H$_5$, —(CH$_2$)$_n$—CH=CH$_2$, —CH$_2$—CONH$_2$, —CH$_2$COOBu$^t$, —(CH$_2$)$_n$CO-heterocyclyl, —CH$_2$—CONH—(CH$_2$)$_n$—COOEt, where n is an integer ranging from 0 to 5.

5. The penam compounds according to claim 1, wherein the heterocycle ring is selected from group: pyrrolyl, pyrrolinyl, imidazolyl, pyrazolyl, pyridyl, pyrimidinyl, pyrazinyl, piperadinyl, oxazolidinyl, thiazolyl, benzothiazolyl, purinyl, pyridazinyl, triazolyl, 4H-1,2,4-triazolyl, 1H-1,2,3-triazolyl or 2H-1,2,3-triazolyl; tetrazolyl, 1H-tetrazolyl, 2H-tetrazolyl; pyrrolidinyl, imidazolidinyl, indolyl, benzimidazolyl, quinolyl, isoquinolyl, indazolyl, benzotriazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, and 1,2,5-thiadiazolyl, optionally further substituted by one or more substituents selected from lower alkyl; lower alkoxy; lower alkylthio; lower alkylamino; cyclo(lower)alkyl; cyclo(lower)alkenyl; hydroxyl; halogen; amino; protected amino; cyano; nitro; carboxy; protected carboxy; sulfo; sulfamoyl; imino; oxo; amino(lower)alkyl and trihalomethyl.

6. The penam compounds of claim 1 selected from the compounds consisting of:
1-{[(2S,3S,5R)-2-Carboxy-3-methyl-4,4,7-trioxo-4-thia-1-azabicyclo[3.2.0]hept-3-yl]methyl}-3-methyl-1H-1,2,3-triazol-3-ium;
1-{[(2S,3S,5R)-2-Carboxy-3-methyl-4,4,7-trioxo-4-thia-1-azabicyclo[3.2.0]hept-3-yl]methyl}-3-ethyl-1H-1,2,3-triazol-3-ium;
1-{[(2S,3S,5R)-2-Carboxy-3-methyl-4,4,7-trioxo-4-thia-1-azabicyclo[3.2.0]hept-3-yl]methyl}-3-n-propyl-1H-1,2,3-triazol-3-ium;
1-{[(2S,3S,5R)-2-Carboxy-3-methyl-4,4,7-trioxo-4-thia-1-azabicyclo[3.2.0]hept-3-yl]methyl}-3-allyl-1H-1,2,3-triazol-3-ium;
1-{[(2S,3S,5R)-2-Carboxy-3-methyl-4,4,7-trioxo-4-thia-1-azabicyclo[3.2.0]hept-3-yl]methyl}-3-(2-amino-2-oxoethyl)-1H-1,2,3-triazol-3-ium and the corresponding acid;
1-{[(2S,3S,5R)-2-Carboxy-3-methyl-4,4,7-trioxo-4-thia-1-azabicyclo[3.2. O]hept-3-yl]methyl}-3-(2-t-butoxy-2-oxoethyl)-1H-1,2,3-triazol-3-ium and the corresponding acid;
1-{[(2S,3S,5R)-2-Carboxy-3-methyl-4,4,7-trioxo-4-thia-1-azabicyclo[3.2.0]hept-3-yl]methyl}-3-(2-morpholin-4-yl-2-oxoethyl)-1H-1,2,3-triazol-3-ium and the corresponding acid;
1-{[(2S,3S,5R)-2-Carboxy-3-methyl-4,4,7-trioxo-4-thia-1-azabicyclo[3.2.0]hept-3-yl]methyl}-3-{2[(2-ethoxy-2-oxoethyl)amino]-2-oxoethyl}-1H-1,2,3-triazol-3-ium and the corresponding acid;
1-{[(2S,3S,5R)-2-Carboxy-3-methyl-4,4,7-trioxo-4-thia-1-azabicyclo[3.2.0]hept-3-yl]methyl}-3-{2-[(3-ethoxy-3-oxopropyl)amino]-2-oxoethyl}-1H-1,2,3-triazol-3-ium and the corresponding acid;
1-{[(2S,3S,5R)-2-Carboxy-3-methyl-4,4,7-troxo-4-thia-1-azabicyclo[3.2.0]hept-3-yl]methyl}-3-(2-{[1-(ethoxycarbonyl)-2-hydroxypropyl]amino}-2-oxoethyl)-1H-1,2,3-triazol-3-ium and the corresponding acid; and 1-{[(2S,3S,5R)-2-Carboxy-3-methyl-4,4,7-trioxo-4-thia-1-azabicyclo[3.2.0]hept-3-yl]methyl}-3-benzyl-1H-1,2,3-triazol-3-ium.

7. A process for the preparation of 2-substituted methyl penam compounds of the formula (I) as claimed in claim 1, which comprises:
reacting a compound of formula (II)

(II)

wherein A=C or N; Het is a five- to six-membered heterocyclic ring with a compound of formula (II b)

R—X                                                              (IIb)

wherein R is as defined above and X represents halogen to produce the compound of formula (I) in the presence or absence of a silylating agent.

8. The process according to claim 7 wherein the silylating agent is present and is selected from hexamethyldisilazane (HMDS), trimethylchlorosilane (TMCS), trimethylsilyl iodide (TMSI), N,O-bis(trimethylsilyl)acetamide (BSA), methyltrimethylsilyltrifluoroacetamide (MSTFA), N,O-bistrimethylsilyltrifluoroacetamide (BSTFA), methyldichlorosilane, dimethyldichlorosilane, diphenyldichlorosilane, N-methylsilylacetamide (MSA), bistrimethylsilylurea and mixture thereof.

9. A pharmaceutical composition comprising at least one of the 2-substituted methyl penam compounds of the formula (I) as claimed in claim 1.

10. A pharmaceutical composition comprising at least one of the 2-substituted methyl penam compounds of the formula (I) as claimed in claim 1 and a pharmaceutically acceptable carrier.

11. The pharmaceutical composition according to claim 9, further comprising an antibiotic agent.

12. The pharmaceutical composition according to claim 11, wherein the antibiotic agent is Penicillin or Cephalosporin derivatives.

13. The pharmaceutical composition according to claim 11, wherein the antibiotic agent is selected from Piperacillin, Ampicillin, Amoxicillin, Bacampicillin, Lenampicillin, Ticarcillin, Amikacin, Gentamycin, Tobramycin, Imipenem, Panipenem, Oxacillin, Aztreonam, Ceftriaxone, Cefbuperazone, Cephalotin, Cefazolin, Cefapirin, Ceftezole, Cefamandole, Cefotiam, Cefuroxime, Cefotaxime, Ceftizoxime, Cefmenoxime, Ceftriaxone, Cefuzoname, Ceftazidime, Cefoperazone, Cefsulodin, Cefoxtin, Cefmetazole, Latamoxef, Cefotetan, Cefbuperazone, Cefminox, Flomoxef, Cephalexin, Cefradine, Cefaclor, Cefadroxil, Cefprozil, Cefuroxime axetil, Cefotiam hexetil, Cefixime, Cefpodoxime proxetil, Ceftibuten, Cefetamet pivoxil, Cefdinir, Cefepime and derivatives thereof.

14. A method of treating bacterial infection in a mammal comprising administering an effective amount of an antibiotic and a compound of the formula (I) as claimed in claim 1.

* * * * *